March 18, 1958 C. F. LEON Plant Pat. 1,692
ROSE PLANT
Filed July 18, 1957
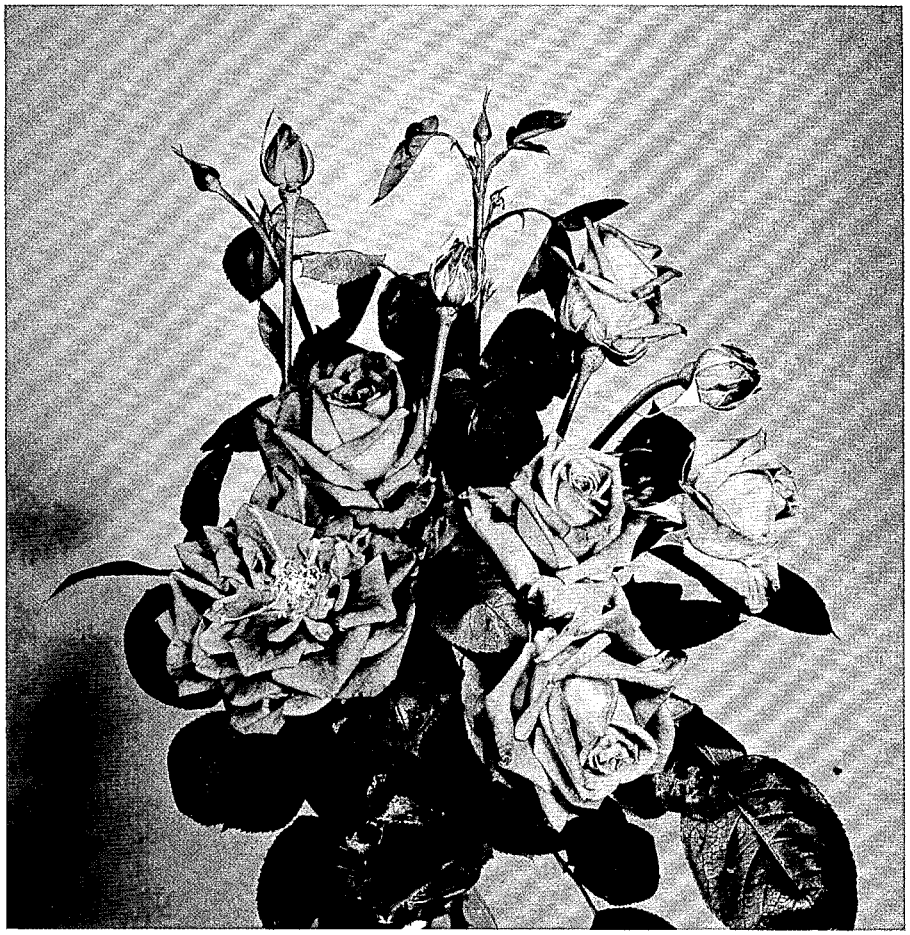
INVENTOR
Charles F. Leon
BY Robb & Robb
ATTORNEYS United States Patent Office Plant Pat. 1,692

Patented Mar. 18, 1958

1,692

ROSE PLANT

Charles F. Leon, Portland, Oreg.

Application July 18, 1957, Serial No. 672,848

1 Claim. (Cl. 47—61)

The present invention relates to a new and distinct variety of rose plant of the hybrid tea class, which was originated by me by crossing an unnamed and unpatented seedling of "Charlotte Armstrong" (Plant Patent No. 455) × "Applause" (Plant Patent No. 829) with the variety "Ena Harkness" (unpatented).

As a result of this breeding, I have produced a new rose variety which is particularly characterized as to novelty by the following distinctive features which, considered together, represent a new and unique combination in a rose of this class:

(1) An upright, vigorous and bushy habit of growth similar to that of the variety "Etoile de Hollande" (unpatented), but less sprawling than the habit of the variety "Crimson Glory" (Plant Patent No. 105);

(2) Relatively large, beautifully formed and gracefully reflexed blooms which are similar in general shape and form to the blooms of the variety "Ena Harkness";

(3) Strong bloom-supporting neck;

(4) Rich, velvety, dark red or crimson general color tonality of the flowers, said color being much darker than that of the blooms of "Ena Harkness"; and (5) Strong fragrance of deep "Old Rose" (centifolia) comparable to that of the variety "Crimson Glory."

Rose experts who have observed my new variety consider the same as constituting a new break in red roses, viz., a very fragrant dark red rose with a strong neck capable of providing good support for the relatively large blooms—something that has not heretofore been available in this color class. Moreover, the new variety is suitable for both garden planting and for use as an exhibition rose when given good cultivation. It is definitely distinguished from its parents as well as from all other varieties of which I am aware, and asexual reproduction thereof by budding, as performed at Roseburg, Oregon, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart, except where general color terms of ordinary dictionary significance are obvious:

Type: Bush; outdoor, seedling; hardy to at least 5° above zero; for cut flowers and for garden decoration.

Class: Hybrid tea.

Breeding: Seedling.

*Seed parent.*—An unnamed seedling of "Charlotte Armstrong" × "Applause."

*Pollen parent.*—"Ena Harkness."

Propagation: Holds its distinguishing characteristics through succeeding propagations by budding.

*Flower*

Locality where grown and observed: Portland, Oregon.

Continuity: Continuous and abundant.

Fragrance: Moderately strong. Nature—"Old Rose perfume" (centifolia).

Flowers borne: Singly and also from 3–5 per stem; in irregular clusters; on strong, long stems.

Quantity of bloom: From moderate to abundant, outdoors.

Bud:

*Peduncle.*—Long; medium heavy; stiff; erect; almost smooth, but with a few Oxblood Red, Plate 00823, p. 191 hairs, although no prickles or thorns. Color—near Scheele's Green, Plate 860/3, p. 175, lightly flushed with Oxblood Red, Plate 00823, p. 191.

*Before calyx breaks.*—Size—medium large; diameter from ¾″ to ⅞″; length from ⅞″ to 1⅛″. Form—pointed; with a conspicuous neck; without foliaceous appendages on the surface of the bud; with slender foliaceous parts of the sepals extending from ⅛″ to ¼″ in length beyond the tip of the bud. Color—near Scheele's Green, Plate 860/3, p. 175, usually darkly flushed with Oxblood Red, Plate 00823, p. 191.

*As calyx breaks.*—Color—near but less blue than Chrysanthemum Crimson, Plate 824/3, p. 169, ranging from near Beetroot Purple, Plate 830/1, p. 173 to near blackish crimson (similar to the coloring of "Crimson Glory" at this stage).

*As first petal opens.*—Size—from medium to medium large; diameter from 1⅞″ to 2″; length from 1¾″ to 2⅛″. Form—long; pointed. Color: outside—near Cardinal Red, Plate 822/1, p. 168, but with a much darker crimson satiny sheen; inside—a much deeper pigment than Cardinal Red, Plate 822/1, p. 168, in addition to having a blackish crimson velvety glow suffusing the inner surface of the petal; occasionally a pure white streak will develop in the center of one of the outer petals similar to those appearing in the roses "Crimson Glory" and "Poinsettia" (unpatented).

*Opening.*—Opens up well in all weather; occasionally in very wet weather, a few inner petals will cling together and delay or retard the opening slightly.

Bloom:

*Size (when fully open).*—From medium to medium large; from 5¼″ to 6″, and occasionally larger on mature plants or when specially fed and watered.

*Petalage.*—From semi-double to double, depending on weather and growing conditions; with stamens showing at all times in the fully open flowers; usually from 24 to 32 petals; arranged regularly.

*Form.*—Full and high-centered at first, but becoming cupped; petals at first being moderately tightly rolled outward, forming a sheath about the heart or center similar to the form of the rose "Ena Harkness," but becoming later at maturity very tightly rolled outward and causing the petals to appear pointed or reflexed.

Petals:

*Texture.*—Moderately thick; somewhat leathery.

*Appearance.*—Inside—velvety. Outside—with a satiny sheen.

*Shape.*—Outside—orbiculate, with from one to several obscure apical notches. Intermediate—orbiculate, with from one to several obscure apical notches. Inside—from orbiculate to ovate, with from one to several obscure apical notches.

This description of a newly opened flower was made from a rose grown outdoors in the month of June, at Portland, Oregon:

*Color.*—Outer petal: outside surface—near Cardinal Red, Plate 822/1, p. 168; inside surface—a much deeper tone than Cardinal Red, Plate 822/1, p. 168, with shadings of near blackish red. Intermediate petal: outside surface—slightly darker than Cardinal Red, Plate 822/1, p. 168; inside surface—somewhat darker than Cardinal Red, Plate 822/1, p. 168, and moderately but irregularly flushed with a much deeper pigment ranging from Beetroot Purple, Plate 830/1, p. 173 to near black, giving blackish velvety gloss to the petals. Inner petal: outside surface—somewhat more intense than Cardinal Red, Plate 822/1, p. 168; inside surface—somewhat richer than Cardinal Red, Plate 822/1, p. 168, but with a more blackish red flush overall, creating a brilliant, deep crimson glow.

This description was made from a rose that was open for three days outdoors in the month of June at Portland, Oregon:

*Color.*—Outer petal: outside surface—slightly lighter than Indian Lake, Plate 826/3, p. 170; inside surface—near Cardinal Red, Plate 822/1, p. 168, but with more bluish black and more intense but not as blue as Chrysanthemum Crimson, Plate 824/3, p. 169, and frequently moderately and irregularly flushed with a much deeper pigment from Beetroot Purple, Plate 830/1, p. 173, to near black; petals also have a small basal flush of from near Tangerine Orange, Plate 9/3, p. 9 to near white. Inner petal: outside surface—similar to outer petal, but more intense; inside surface—similar to outer petal, but much more intense and having a rich, velvety glow.

*General color effect.*—Newly opened flower—a rich, velvety crimson, with lighter tones of Cardinal Red, Plate 822/1, p. 168, shaded with darker pigments not quite as blue as Chrysanthemum Crimson, Plate 824/3, p. 169. Three days open—rich Cardinal Red, Plate 822/1, p. 168, but darker and more intense, with dusky dark pigments similar to Beetroot Purple, Plate 830/1, p. 173; does not blue as much at this stage as "Crimson Glory."

*Behavior.*—Usually drops off cleanly; fading slightly to near Indian Lake, Plate 826/3, p. 170, with occasional browning of the inner petals in wet weather; tips of outer petals turn to blackish brown tones in muggy, wet weather.

*Flower longevity.*—On bush in garden—from 3 to 5 days in June. Cut roses grown outdoors and kept at living-room temperature—3 or 4 days in June; in cooler weather, such as in the months of September and early October, the blooms keep from 1 to 3 days longer both indoors and outdoors.

*Reproductive organs*

Stamens: From medium number to many; arranged regularly about pistils. Color—near Rose Red, Plate 724, p. 158.

Filaments: Medium length: from 7/16" to 1/2" long; mostly all with anthers; usually from 118 to 128 filaments. Color—near Rose Red, Plate 724, p. 158.

Anthers: Medium size; mostly open at once. Color—near Yellow Ochre, Plate 07/2, p. 101.

Pollen: From moderate to abundant. Color—golden yellow.

Pistils: Many; usually ranging from 143 to 147 or slightly higher.

Styles: Uneven; from 5/16" to 9/16" in length; loosely bunched.

Stigma: Slightly greyish-white.

Ovaries: All enclosed in calyx.

Hips: Similar in shape to those of the rose "Damascena" (unpatented); with a conspicuous neck from 7/8" to 1 1/8" in diameter and from 5/8" to 7/8" in height; moderately smooth; walls from medium thick to medium fleshy. Color—varying shades of green ranging in tone from near Parsley Green, Plate 00962/1, p. 193 to near Scheele's Green, Plate 860/3, p. 175 as ripening progresses, with yellow and often reddish overtones.

Sepals: Permanent; moderately long; spear-shaped; recurved; from 1 5/8" to 2" long and from 1/2" or more in width at base. Color—near Scheele's Green, Plate 860/3, p. 175, but generally lightly flushed with light tones of Oxblood Red, Plate 00823, p. 191 near the tips of the sepals.

Seeds: Few; medium size; from 7 to 14 per hip, with average about 9.

*Plant*

Foliage:

*Leaves.*—Compound of 3 to 7 leaflets, mostly in units of 5; moderately abundant, ranging from 10 to 15 sets of leaflets on vigorous shoots; medium large, with apical leaflets ranging in size from 2" x 2 3/4" to 2 5/8" x 3 3/4" or larger; moderately heavy; leathery; with a slight glossy tinge.

*Leaflets.*—Shape—from ovoid to slightly more rounded oval, with apex having a slightly though easily perceptible acuminate tip. Base—rounded. Margin—generally regularly serrate.

*Color.*—Mature: upper surface—between Parsley Green, Plate 00962/1, p. 193 and Spinach Green, Plate 0960/1, p. 187; under surface—near Willow Green, Plate 000862/1, p. 199, but greener and less grey. Young: upper surface—near Garnet Brown, Plate 00918/1, p. 192, later flushed green from center rib to main veins; under surface—near Oxblood Red, Plate 00823, p. 191.

*Rachis (the supporting stem of the compound leaf.*—Medium heavy. Upper side—single groove, with a few marginal glandular cilia. Under side—moderately smooth, with sparsely thorny surface.

*Stipules.*—Overall size ranging from 3/16" x 5/8" to 5/16" x 1 7/16" or larger; with long, narrow points ranging in length from 1/4" to 3/8" and turning outward, generally at an angle less than 45°; very seldom recurving towards the stem.

*Disease resistance.*—No susceptibility to blackspot as observed in test plots at Portland or Roseburg, Oregon, although somewhat susceptible to mildew on young foliage under certain weather conditions, particularly in cases of a combination of cold nights of around 40° and warm days of around 75° or more, but not as susceptible to mildew as the variety "Crimson Glory"; resistance to mildew comparable to that of the rose "Ena Harkness," as determined from comparison with that variety when grown under comparable conditions in Portland and Roseburg, Oregon; no rust, canker or other fungus diseases have been observed to date in the test plantings.

*Insect resistance.*—Inherent vigor quickly overcomes severe slug damage to shoots and canes, but no unusual resistance to insect attacks has been established.

Growth:

*Habit.*—Upright; bushy; with moderately many branches; ranging from 38" to 48" in height or taller, according to age.

*Growth.*—Very vigorous; similar to or surpassing the rose "Etoile de Holland."

*Canes.*—From moderately heavy to heavy; ranging from 1/2" to 5/8" in diameter or larger.

*Main stems.*—Color—dull grey green at maturity. Thorns—many; ranging from 37 on 15" stems to 77 on 24" stems; medium large (3/8" x 3/16" at base and from 1/2" to 5/8" in length); hooked downwards; color — light tan at maturity. Prickles—few; color—grey green. Hairs—very few; color—grey green.

*Branches.*—Color—dull grey green at maturity; with occasional flushes of Oxblood Red, Plate 00823, p. 191, or Garnet Brown, Plate 00918/1, p. 192, according to various stages of maturity. Thorns—decreasing in number from those on main stems to only several; medium size; hooked downward; with narrow base. Prickles—few; color—grey green. Hairs—few; color—slight greenish grey according to maturity.

*New shoots.*—Color—from bright brownish red to near Garnet Brown, Plate 00918/1, p. 192, similar to color of young foliage. Thorns—moderately few; medium long; hooked downward; with narrow, slightly oval base. Prickles—few; color—reddish tones near Garnet Brown, Plate 00918/1, p. 192. Hairs—very few; color—reddish tones.

I claim:

A new and distinct variety of rose plant of the hybrid tea class, substantially as herein shown and described, characterized particularly as to novelty by its upright, vigorous and bushy habit of growth, its relatively large, beautifully formed and gracefully reflexed blooms, its strong bloom-supporting neck, the rich velvety dark red general color tonality of its blooms, and the relatively strong, deep "Old Rose" fragrance of the blooms.

No references cited.